(12) United States Patent
Bink et al.

(10) Patent No.: US 8,321,147 B2
(45) Date of Patent: Nov. 27, 2012

(54) STATISTICAL APPROACH FOR OPTIMAL USE OF GENETIC INFORMATION COLLECTED ON HISTORICAL PEDIGREES, GENOTYPED WITH DENSE MARKER MAPS, INTO ROUTINE PEDIGREE ANALYSIS OF ACTIVE MAIZE BREEDING POPULATIONS

(75) Inventors: Marinus C. A. M. Bink, Wageningen (NL); Carl J. F. ter Braak, Bennekom (NL); Oscar S. Smith, Redwood City, CA (US); L. Radu Totir, Johnston, IA (US)

(73) Assignees: Pioneer Hi-Bred International, Inc, Johnston, IA (US); Wageningen University, Wageningen (NL); Stichting Dienst Landbouwkundig Onderzoek, Wageningen (NL)

( * ) Notice: Subject to any disclaimer, the term of this patent is extended or adjusted under 35 U.S.C. 154(b) by 517 days.

(21) Appl. No.: 12/572,663

(22) Filed: Oct. 2, 2009

(65) Prior Publication Data
US 2010/0095394 A1 Apr. 15, 2010

Related U.S. Application Data

(60) Provisional application No. 61/102,144, filed on Oct. 2, 2008.

(51) Int. Cl.
*G06F 19/00* (2011.01)
*A01H 1/00* (2006.01)
(52) U.S. Cl. ......................................... 702/19; 800/260
(58) Field of Classification Search .................... None
See application file for complete search history.

(56) References Cited

U.S. PATENT DOCUMENTS
6,399,855 B1 6/2002 Beavis
2005/0144664 A1 6/2005 Smith

FOREIGN PATENT DOCUMENTS
WO WO 01/49104 A2 7/2001

OTHER PUBLICATIONS ter Braak, et al., "Extending Xu's (2003) Bayesian Model for Estimating Polygenic Effects Using Markers of the Entire Genome", Genetics: Published Articles Ahead of Print, published May 23, 2005 as 10.1534/genetics.105.040469. 10 pages.
ter Braak, et al., "Approximating a similarity matrix by a latent class model", Manuscript for submission to Computational Statistics and Data Analysis, Oct. 16, 2007. 17 pages.
Pritchard, et al., "Inference of Population Structure Using Multilocus Genotype Data", Genetics 155:945-959 (Jun. 2000). 15 pages.
"FlexQTL(tm)—Quantitative Genetics on Pedigreed Populations", http://www.biometrics.wur.nl/UK/Software/FlexQTL/ (1 of 5)Oct. 2, 2007. 4 pages.
Falush, et al., "Inference of Population Structure Using Multilocus Genotype Data: Linked Loci and Correlated Allele Frequencies", Genetics, 164:1567-1587 (Aug. 2003). 22 pages.
Bink, et al., "Multiple QTL mapping in related plant populations via a pedigree-analysis approach", Theor. Appl; Genet 104:751-762 (2002). 12 pages.
Bink, "FlexQTL"—summary and follow-up on discussion with Howie (visit Wag, 26-28-sep), Plant Research International, Wageningen, UR, slide presentation. 77 pages.
Bink, et al., "Fine mapping of quantitative trait loci using linkage disequilibrium in inbred plant populations", Euphytica, 137:95-99 (2004). 5 pages.
Bink, Marco, "A Bayesian approach to map multiple QTL in pedigreed plant breeding populations", U.S. Department of Statistics News and Discussion: Marco Bink, Apr. 30, 2007. 2 pages.

*Primary Examiner* — John S Brusca
(74) *Attorney, Agent, or Firm* — Potter Anderson Corroon LLP

(57) ABSTRACT

This invention provides a novel means of predicting plant phenotypes that incorporates previously unusable dense marker data derived from historical pedigrees. The method operates by collecting information from a population pertaining to one or more loci, which is used to build one or more matrices by calculating, for the alleles present at the measured loci, the probability that the alleles are identical by descent. These matrices are then used to develop a second set of one or more matrices in which each value represents the probability that a certain individual in the population descended from a certain ancestral (founder) genotype. This set of second matrices can then be used as part of a breeding program for selecting and breeding individuals from the population or can be used to better classify the individuals in the population, leading to improved plant phenotypes.

17 Claims, 7 Drawing Sheets

STATISTICAL APPROACH FOR OPTIMAL USE OF GENETIC INFORMATION COLLECTED ON HISTORICAL PEDIGREES, GENOTYPED WITH DENSE MARKER MAPS, INTO ROUTINE PEDIGREE ANALYSIS OF ACTIVE MAIZE BREEDING POPULATIONS

CROSS-REFERENCE TO RELATED APPLICATIONS

This is a non-provisional of U.S. Patent Application Ser. No. 61/102,144 filed Oct. 2, 2008, the contents of which are herein incorporated by reference in their entirety.

BACKGROUND

The manipulation of crop genetics for the optimization of agronomic traits has resulted in a revolution in the seed industry. However, as many as 98% of these agronomic traits are quantitative traits, such that they are controlled by two or more genes and have measurable variability among the individual phenotypes. In order to understand and control the inheritance of these genes and the resultant phenotypes, scientists in the field have traditionally utilized methods such as quantitative trait locus (QTL) analysis.

As an outcome of QTL analysis, scientists identify chromosomal regions that are in close proximity to genes controlling a trait of interest. These chromosomal regions may be the target gene itself or may be genetic markers such as RFLPs, AFLPs, RAPDs, VNTRs, microsatellite polymorphisms, SNPs, and STRs. Because the markers are in close proximity to the genes, they tend to be inherited along with the gene (a phenomenon known as genetic linkage). As a result, the marker can be used to track the inheritance of the genes of interest. The process and statistical methods used to identify the location and effects of the various genes of interest or markers associated with these genes is called QTL mapping.

A major limitation of QTL analysis is that it has historically been limited to populations derived from single crosses of inbred lines and thus has not incorporated the extensive plant pedigree data that has been collected by plant breeders. Previous attempts to explicitly include this information have proven to be computationally intensive and are difficult to parameterize. As a result, vast amounts of data collected over the course of the development of modern elite plant varieties is essentially unused for purposes of phenotypic prediction.

Analysis of more complex populations derived from multiple founders or collected from ongoing breeding programs has the potential to significantly improve the understanding of important agronomic traits. For example, if the stability and magnitude of individual genes across different genetic backgrounds can be quantified more accurately, improved response to selection can be obtained. The use of these more complex populations would provide better context for making inferences by better approximating commercial breeding populations and would increase cost effectiveness by allowing use of available phenotypes from ongoing selection experiments. While some efforts have been undertaken to use historical pedigree data to predict phenotypes within mapping populations, those efforts have been largely unproductive in large part because of the inability to efficiently use the extensive pedigree and marker information that must be combined and analyzed.

The important benefits that can be derived from incorporation of comprehensive pedigree data coupled with the inability of those skilled in the art to effectively perform such analysis underscores the long felt, unsatisfied need for such tools in the art.

SUMMARY

This invention provides a novel means of predicting plant phenotypes that incorporates previously unusable dense marker data derived from historical pedigrees. The method operates by collecting information from a population pertaining to one or more loci. The information is then used to build one or more matrices by calculating, for the alleles present at the measured loci, the probability that the alleles are identical by descent (IBD). These matrices are then used to develop a second set of one or more matrices in which each value represents the probability that a certain individual in the population descended from a certain ancestral (founder) genotype. This set of second matrices can then be used as part of a breeding program for selecting and breeding individuals from the population or can be used to better classify the individuals in the population, leading to better identification of improved plant phenotypes. The disclosed methods take the full amount of historical pedigree and marker data that is available or desired to be utilized for predictive purposes and places it into a manageable form such that it may be used to improve the mapping resolution while still making the analysis of the information practical from a processing perspective. As a result, this method results in better mapping resolution and higher prediction accuracy than has been realistically feasible.

The genetic markers used can be any that are used in traditional QTL mapping analysis such as RFLPs, AFLPs, RAPDs, VNTRs, microsatellite polymorphisms, SNPs, and STRs. The phenotypic traits include any polygenic phenotypic traits of interest.

In one embodiment of the invention, the population consists of diploid plants, either hybrid or inbred. In another embodiment, the population consists of polyploid plants. Plants relevant to the invention include, for example, maize, wheat, rice, millet, barley, sorghum, rye, soybean, alfalfa, oilseed Brassica, cotton, sunflower, potato, or tomato.

The first matrix (of IBD probabilities) is calculated using standard statistical techniques, including those based on Markov Chain Monte Carlo algorithms. The genotypes in the second matrix are automatically generated using mathematical models. In a preferred embodiment, the second matrix is calculated using a latent (ancestral) class model, although other models such as a threshold model, distance model, a vector model, or a cluster analysis model may be used. In a preferred embodiment, the second matrix is used in a Bayesian statistical approach for more accurate QTL detection and prediction of plant phenotypes with calculations performed using a Markov Chain Monte Carlo based algorithm while keeping computational efforts to a minimum. These calculations may also be computer-implemented.

DETAILED DESCRIPTION

Figure 1:
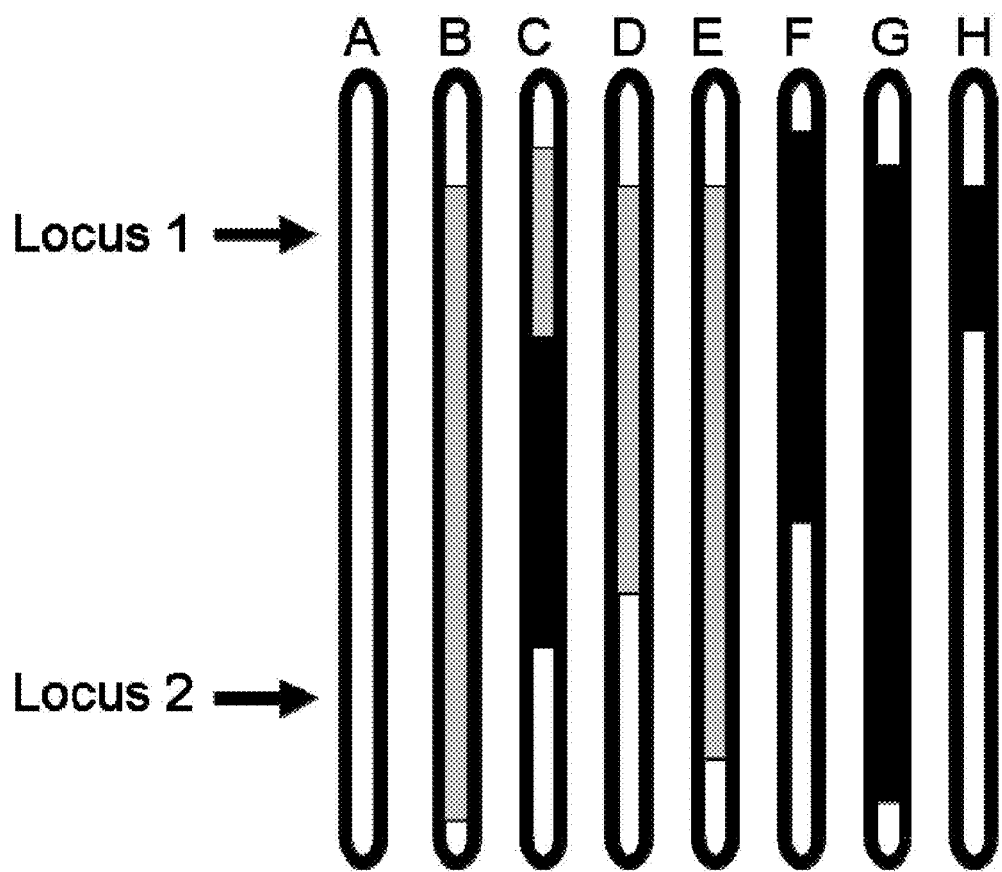
FIG. 1 is a graphical depiction of chromosomal position of two different loci in a population of eight individuals.

The present invention incorporates population pedigree data and associated genetic marker data in order to better predict group characteristics (e.g. phenotypes) within the population. This is accomplished, for example, through the use of two matrices. While matrices are used herein, it is understood that alternative methods may also be used to achieve the same result.

The elements of the first matrix (Q) represent the probability that pairs of alleles are identical by descent. Alleles are identical by descent (IBD) if they are identical copies of an allele segregating from a common ancestor within the defined pedigree. In the context of inbred lines, allele and individual are exchangeable. As such, Q is an n×n square symmetric matrix of non-negative elements between 0 and 1, where n represents the number of individuals in the population. The first matrix depends on the specified locus and is typically calculated from the pedigree data and genetic marker data. The matrix may also contain identity by descent probabilities measured across multiple loci, chromosomal segments, haplotypes, or the whole genome.

The second matrix (P) is an n×K matrix comprised of non-negative elements that represent the assignment probabilities of individuals to classes (e.g. ancestral genotypes), wherein K represents a fixed but unknown number of classes and every row of P sums to 1. With this arrangement, the second matrix represents the first matrix in the sense that Q is approximated by $PP^T$, while disregarding the diagonal elements of Q and $PP^T$. Example matrices for Q and P are found in Table 1 below:

TABLE 1

Artificial 6 × 6 Q matrix for six individuals labeled A-F and a 6 × 4 matrix P with classes labeled $C_1$-$C_4$, giving a perfect fit to the off-diagonal elements of Q by the formula $PP^T$.

|   |   | A | B | C | D | E | F |   |   | $C_1$ | $C_2$ | $C_3$ | $C_4$ |
|---|---|---|---|---|---|---|---|---|---|---|---|---|---|
|   | A | 1 | 0 | 0 | 0 | 0 | 0 |   | A | 1 | 0 | 0 | 0 |
|   | B | 0 | 1 | 1 | 1 | 0 | 0 |   | B | 0 | 1 | 0 | 0 |
| Q = | C | 0 | 1 | 1 | 1 | 0 | 0 | P = | C | 0 | 1 | 0 | 0 |
|   | D | 0 | 1 | 1 | 1 | 0 | 0 |   | D | 0 | 1 | 0 | 0 |
|   | E | 0 | 0 | 0 | 0 | 1 | 0.7 |   | E | 0 | 0 | 1 | 0 |
|   | F | 0 | 0 | 0 | 0 | 0.7 | 1 |   | F | 0 | 0 | 0.7 | 0.3 |

This approximation can be accomplished through methods such as, but not limited to, least squares using a number of numerical approaches, such as a brute force genetic algorithm (differential evolution) or two different iterative row-wise quadratic programming approaches. Alternatively P can be constrained to contain values 0 and 1 only, representing a fixed grouping of individuals.

The utility of the second matrix (P) is manifold (but not limited to):
1. The matrix P is much smaller in size than the matrix Q if K<n which makes it easier to deal with both for human inspection and for computer representation.
2. The matrix P gives an explicit probabilistic representation of inheritance of alleles of individuals from a set of latent (ancestral) founders. The elements of P have a clear meaning; they are the identity by descent probabilities of the n individuals at a specified locus with the K latent ancestors.
3. Each row of P is associated with a specified individual and indicates the number of ancestors that effectively contributed to the genotype of that individual at a specified locus;
4. The value of K that gives a good approximation to Q indicates the number of ancestors that actually contribute to the genotype of the individuals at a specified locus.
5. In many cases in which a pedigree is available the latent ancestors can be identified as being the most recent common ancestors in the pedigree.
6. The matrix P makes it possible to sample or draw ancestors for each of the n individuals in such a way that the probability that individual i and j have a common ancestor is their identity by descent probability for all i≠j (i=1, . . . , n; j=1, . . . , n). Each such sample is an explicit possible way of inheritance of the individuals from the set of latent ancestors.

Utilities 2 and 6 are of foremost importance in regression approaches with genetic predictors (Malosetti et al, 2006) and in Bayesian methods (Bink et al. 2008) for QTL analysis that cannot work with the first matrix or matrices (Q) directly. Utility 2 makes it possible to calculate genetic predictors (matrix P), the probability density for a proposed way of inheritance. Utility 6 makes it possible to generate proposals for ways of inheritance.

Developing a Latent Ancestral Class Model for an Identity by Descent Matrix

As previously stated, we begin with an n×n square symmetric matrix (Q) with elements $q_{ij}$ between 0 and 1, denoting the probability that the alleles of a pair of individuals i and j (i=1, . . . , n; j=1, . . . , n) at a specified locus are identical by descent, that is, inherited from the same ancestral allele. The matrix Q depends on the position of the locus on the chromosome, but is fixed when a specified locus is considered. The goal is to develop a model that has an explicit, possibly probabilistic, representation for the inheritance of the allele of each individual from a common set of ancestral founders, but without further usage of the pedigree and/or marker data. The pedigree and/or marker data is used to generate the matrix Q. The matrix Q thus condenses all information about the pedigree and marker data that we can use in the following. Because there is no pedigree information beyond the information contained in the matrix Q, the ancestral founders of the intended model are unknown and therefore "latent" as they can only be hypothesized. The intended model is the latent ancestral class model developed here.

Using this approach, we arrive at a model in which the allele of each individual is inherited from a single latent ancestor. The transitivity property applies to this problem such that if the alleles for individuals i and j are inherited from the same ancestor, and the alleles for individuals i and k are inherited from the same ancestor, then the alleles for individuals j and k are inherited from the same ancestor.

We extend this inheritance model with probabilities. Let P be an n×K matrix with K the number latent ancestors and elements $p_{ik}$ being the probability that the allele of individual i is inherited from ancestor k. Note that $$p_{ik} \geq 0 \text{ and } \sum_{k=1}^{K} p_{ik} = 1 \quad (1)$$

$$(i = 1, \ldots, n; k = 1, \ldots, K).$$

In this model we do not know whether the allele of individual i is inherited from ancestor k, but only the probability of this inheritance. On assuming independence of inheritance for each pair of individuals, the probability that individuals i and j inherited from the same ancestor is, according to the model, $$q_{ij}^* = \sum_{k=1}^{K} P(i \in \text{class}(k) \wedge j \in \text{class}(k)) = \sum_{k=1}^{K} p_{ik} p_{jk} \forall i \neq j. \quad (2)$$

Mathematically, the $\{q^*_{ij}\}$ are coincidence probabilities induced by a latent class model with memberships probabilities P.

As a result, we wish to find a matrix P such that $q^*_{ij}$ is close to the observed $q_{ij}$; for all $i \neq j$. This can be solved using a least-squares approximation such that the problem is to minimize the loss function:

$$f(P) = \sum_{i=1}^{n} \sum_{j=i+1}^{n} (q_{ij} - p_i^T p_j)^2, \quad (3)$$

where $p_i^T$ denotes the $i^{th}$ row of P, subject to the nK non-negativity and n equality constraints in Equation (1).

The loss can be reported in terms of the root mean squared error (RMSE), defined as:

$$\sqrt{2f(P)/(n(n-1))}.$$

If the loss is small, we have thus obtained an explicit inheritance model for the alleles of the individuals that accurately approximate the identity by descent probabilities as given by the matrix Q, which was calculated from the available pedigree and/or marker information. The inheritance probabilities of alleles of individuals from latent ancestors are given in the matrix P. The key identity to arrive at identity by descent probabilities is equation (2) which can also be written in matrix notation as $Q^* = PP^T$ while disregarding the diagonal elements of $Q^*$. Here $Q^*$ is the approximation of Q. Note that equation (2) also holds true if the elements of P are only 0 or 1, and thus P represents a division of the individuals into disjoint groups. In this case, P can in principle be derived from any method of cluster analysis applied to Q; otherwise any form of fuzzy clustering can be applied. Here we develop specialized methods to obtain the best P to approximate Q by $PP^T$.

The loss function set forth in equation (3) is not convex which raises the possibility of multiple local minima, even beyond local minima generated by rearrangement of the columns of P. As a result, a global optimization method is required. A differential evolution approach and two versions of iterative row-wise quadratic programming approaches will serve as three examples of such methods.

Global Optimization Using a Differential Evolution Approach

Differential Evolution (DE) is a derivative-free global optimization method that belongs to the family of evolutionary algorithms. In DE a population of solution vectors $x_1 \ldots x_N$ is used to explore the solution space and is maintained for a number of generations until the population reaches the minimum. In our example, each member vector $x_i = \text{vec}(P_i)$ with $P_i$ a trial solution of (3) subject to (1). The size of the population depends on the problem and the other parameters of the differential evolution, but in general it should be higher than the number of parameters d. For this example N=2d=2nK is used.

Each member's vector $x_i$(i=1 . . . N) can be initialized independently with nK random values between 0 and 1. The K values of each of the n individuals can be divided by their sum so as to satisfy constraints (1). The exploration of the space is carried as follows in DE.

A new "mutant" vector is proposed for each member vector $x_i$ by using three different randomly selected vectors of the population:

$$x^*_i, x_{r_0} + F(x_{r_1} - x_{r_2}) \quad (4)$$

where F is a scalar that determines step size.

In addition to (4), another generic operation is used in DE, namely crossover. With a crossover rate CR (0<CR≦1), a fraction CR of the elements in $x_i$ are mutated according to (4), whereas the remaining parameters are left unchanged, i.e. are set equal to the corresponding values in $x_i$.

In this algorithm, the crossover operation is applied on the level of the individuals within the parameter vector, i.e. the parameters of an individual are either mutated according to (4) or left unchanged. In terms of $P_i$, each row of $P_i$ is thus independently selected for mutation, the selection probability being CR.

To ensure that the resulting mutant vector satisfies the constraints of (1), any negative value in $X^*_i$ is replaced with 0, any value greater than 1 is replaced with 1, and the resulting K elements of each of the n individuals in $x^*_i$ are divided by their sum.

After the aforementioned adjustments, the member vector $x_i$ is replaced by $x^*_i$ if $f(x^*_i) \leq f(x_i)$ where $f(.)$ is the loss function. Each possible update of $x_i$ requires one function evaluation at the time that loss function values of members are stored.

Global Optimization Using Iterative Row-Wise Quadratic Programming

Another method to minimize the loss function $f(P)$ is to use iterative row-wise quadratic programming. When using quadratic programming, $f(P)$ is minimized over $p_i$ while keeping the other rows of P fixed, which can be achieved by minimizing:

$$\|q_i - P_{-i} p_i\|^2 \quad (5)$$

where $q_i$ is the $i^{th}$ column of Q without $q_{ii}$, and $P_{-i}$ denotes matrix P after deleting row i subject to the constraints $p_i \geq 0$ and $p_i^T 1 = 1$ where 0 and 1 denote vectors of appropriate lengths with all zero and unit elements respectively. Problem (5) can be recognized as one of quadratic programming. We developed two specialized approaches for this problem, called Approach A and Approach B.

With an algorithm to fit a single row, the complete algorithm for fitting P to Q is:

Complete Algorithm:

(1) Initialize P, e.g. with each row filled with random uniform numbers between 0 and 1, which are then divided by their sum, so as to satisfy the constraints (1).

(2) While $f(P)$ decreases:

For i=1, N minimize $f(P)$ over the ith row $p_i$, while keeping the other rows of P fixed, by, for example, Approach A or Approach B.

We now provide details of Approach A and Approach B.

Approach A for Global Optimization Using Iterative Row-Wise Quadratic Programming The constraint $p_i^T 1=1$ can be enforced by reparamaterization to yield $p_i = Uv + \alpha 1$ with U a column wise orthonormal basis for the orthocomplement of 1, and v and $\alpha$ a vector and scalar respectively. Because U and 1 jointly span the whole space, the vector v and scalar $\alpha$ always exist. Now the constraint that $p_i^T 1=1$ implies that $vU^T 1 + \alpha 1^T 1 = 1$, and because $U^T 1 = 0$ and $1^T 1 = K$, it follows that $\alpha = K^{-3}$. Hence $p_i = Uv + K^{-1} 1$ which satisfies the constraint $p_i^T 1 = 1$ for every v.

Based on reparameterizing $p_i$ as above, it remains to minimize the function:

$$g(v) = \|q_i - P_{-i} K^{-1} 1 - P_{-i} U v\|^2$$

over v subject to the constraint that $Uv + K^{-1} 1 \geq 0$. This in turn can be solved by minimizing $h(v) = \|f - Ev\|^2$ subject to $Gv \geq h$, where:

$$f = q_i - K^{-1} P_{-i} 1$$

$$E = P_{-i} U$$

$$G = U$$

$$h = -K^{-1} 1.$$

Once the optimal v is found (see Lawson and Hanson 1995), the vector $p_i$ that minimizes $f(P)$ over $p_i$ is given by $Uv + K^{-1} 1$.

Approach B for Global Optimization Using Iterative Row-Wise Quadratic Programming As each row of P sums to unity, a column of P can be deleted as we show now. We delete the last column, i.e. column K. With the (K-1)-vector $b = (p_{i1}, p_{i2}, \ldots, p_{i(K-1)})^T$. We can write $$p_i = [b^T, 1 - b^T 1_{(K-1)}]^T = Cb + d \quad (6)$$

with K-vector $d = (0 \ldots 0, 1)^T$, with the "1" in position K, and K×(K-1) matrix $$C = \begin{bmatrix} I_{K-1} \\ -1_{K-1} \end{bmatrix},$$

where $I_{K-1}$ is a (K-1)×(K-1) identity matrix and $1_{K-1}$ is a (K-1)-vector of ones Then by inserting (6) in (5) for both $p_i$ and each row of $P_{-i}$ and by defining the (N-1)×(K-1) matrix X with elements $x_{jk} = p_{jk} - p_{jK}$ and the N-1 vector y with elements $y_j = q_{ij} - p_{jK}$ for j=1, ..., i-1, i+1, N and k=1 ... (K-1), we arrive at the following equivalent problem: find b so as to $$\text{minimize } \|y - Xb\|^2 \text{ subject to } b_k \geq 0 \text{ and } \sum_{k=1}^{K-1} b_k \leq 1. \quad (7)$$

After having found the solution to problem (7), we obtain the solution to problem (5) by back-transformation of (6), namely $P_{ik} = b_k$ for k=1, ..., K-1 and $$p_{iK} = 1 - \sum_{k=1}^{K-1} b_k.$$

There are several ways to solve problem (7) because it is a standard quadratic program. We mention in particular the LSI algorithm in Lawson and Hanson (1974).

Methods to Choose K

Two approaches to choose K in the latent ancestral class model are as follows. In the first approach, we minimize the Akaike information criterion (AIC) which for unknown variance is defined as $AIC = N \log(f(P)) + 2p^*$ with $N = n(n-1)/2$, the number of observations, and $p^* = n(K-1)$, the number of parameters. In the second approach we perform two steps: first set the number of ancestral classes equal to its maximum (the number of columns in Q); second determine how many columns of the matrix P contain nonzero elements (representing the actual number of latent ancestors that most accurately reproduce Q). An alternative to the second step in the second approach is to use the matrix P to calculate the effective number of the latent ancestors by using the equation $$n_{\text{eff}} = 1 \Big/ \sum_{k=1}^{K} (p_{+k} / p_{++})^2 \quad (\text{HILL 1973})$$

where + as index indicates the sum over the index; for example $p_{+k}$ is the column sum. Note that $1/n_{\text{eff}}$ is equal to Simpson's index (HILL 1973). The Simpson index can be interpreted in our context as the probability that two randomly chosen individuals inherited from the same ancestor. Notice that the number of latent ancestors and the effective number of latent ancestors can also be usefully defined for the $i^{th}$ individual by the number of nonzero elements in the vector $p_i$ and $$\text{by } n_{\text{eff},i} = 1 \Big/ \sum_{k=1}^{K} p_{ik}^2,$$

respectively. Notice also that each column sum of P contains the expected number of the individuals that inherit from the corresponding latent ancestor.

Usage of the Latent Ancestral Class Model in QTL Analysis

In QTL analysis using (mixed model) regression analysis with genetic predictors (Malosetti et al., 2006) the matrix P can directly be inserted as a, possibly additional, set of K genetic predictors. The use of matrix P in this framework can be more efficient in statistical and computational aspects than the use of matrix Q in a variance components implementation.

QTL analysis using Bayesian methods (Bink et al., 2008) can in theory utilize the full pedigree and marker data. In such an approach, QTL alleles are a priori independently assigned to the actual founders of the pedigree where the number of alleles is two or more (Bink et al., 2008). However, the numerical implementation by a Markov Chain Monte Carlo algorithm (Bink et al., 2008) is impractical, as it requires more computing resources and time than is available in practice. One solution is to delete a large part of the pedigree and a priori independently assign alleles to the founders of the remaining part of the pedigree, which we call parents from now on. However, this solution ignores the left-out part of the pedigree and neglects the fact that alleles of different parents are not necessarily independent. An alternative is to replace the pedigree and marker information at each locus on the genome by an identity by descent matrix (Q) among the parents. With n parents, each Q matrix is of size n by n. However, identity by descent matrices cannot directly be used in oligogenic Bayesian methods for QTL analysis whereas, possibly probabilistic, pedigree information can be used. A latent ancestral class model provides probabilistic information that can be used. The fact that actual founders are replaced by latent (hypothesized) ancestors does not hamper this usage. Note that the latent ancestral class model is constructed to contain as much of the pedigree and marker information as possible. In the Bayesian analysis the assumption that the alleles of the parents are independent (which discards the left-out pedigree information) is replaced by the assumption that the alleles are inherited according to the latent ancestral class model as follows: the cut-down pedigree (in which the parents become founders) is extended implicitly through the use of the P matrices towards the K ancestors. The alleles of these ancestors are a priori independent and the parents inherit their alleles from these ancestors with probabilities specified in the matrix P. This completes the Bayesian model description.

One example of a numerical implementation of the modified Markov Chain Monte Carlo algorithm for this model is as follows. The algorithm proceeds by Gibbs steps whereas each Gibbs step contains a proposal and a Metropolis-Hastings accept-reject step. The proposal consists of both a new QTL location and a new set of alleles for latent ancestors and parents. The new QTL location is drawn from a symmetric distribution centered at the current QTL location. The alleles for the latent ancestors are drawn independently from the prior distribution. The new set of alleles for the parents is drawn by first sampling from the appropriate P matrix from which ancestor each parent inherited and then assigning, for each parent, the allele (of the ancestor) that it inherited. As this proposal samples from the prior distribution for ancestral and parental alleles and is symmetric in the old and new QTL position, the Metropolis-Hastings acceptance ratio is simply a ratio of the likelihoods of the current and proposed values.

There is an additional detail that needs description. We may not have access to the matrix P for the proposed QTL location, but only to two flanking positions. Let $P_l$ and $P_r$ be the P-matrices pertaining to the flanking positions $\lambda_l$ and $\lambda_r$. Then, the P-matrix at the QTL position $\lambda$ $$P_\lambda = \begin{cases} P_l & \text{with probability } (\lambda - \lambda_l)/(\lambda_r - \lambda_l) \\ P_r & \text{with probability } (\lambda_r - \lambda)/(\lambda_r - \lambda_l) \end{cases} \quad (11)$$

Sampling from $P_l$ and $P_r$ with these probabilities yields precisely the average IBD probabilities $Q_\lambda = ((\lambda - \lambda_l)Q_r + (\lambda_r - \lambda)Q_r)/(\lambda_r - \lambda_l)$ if $P_l$ and $P_r$ perfectly fit $Q_l$ and $Q_r$, respectively. In the case of a perfect fit, the sampling approach of equation (11) is therefore equivalent to that of calculating the P matrix corresponding to $Q_\lambda$. In the case of a non-perfect fit, the two approaches are not quite equivalent but close, especially when the interval between the flanking positions is narrow, as is typically the case for the parents. Note that the sampling approach is not the same as sampling from a weighted average of $P_l$ and $P_r$. Also, the average IBD probabilities $Q_\lambda$ can be obtained via sampling of the two neighboring IBD matrices $Q_l$ and $Q_r$, similar to (11), i.e., $$Q_\lambda = \begin{cases} Q_l & \text{with probability } (\lambda - \lambda_l)/(\lambda_r - \lambda_l) \\ Q_r & \text{with probability } (\lambda_r - \lambda)/(\lambda_r - \lambda_l). \end{cases}$$

Practical Advantage of the Disclosed Methods

In practice, the matrices used will incorporate information that has been compiled regarding the pedigree of potential parental lines for each biparental cross. While more pedigree information is preferred, the above-described method is still beneficial if only a portion of the relevant pedigree information is known, or if only a portion of the relevant pedigree information is used for ease of analysis. One of the advantages of the disclosed method is a reduction in the need to discard portions of relevant pedigree data in the interest of processing resources. In effect, the disclosed method allows the available pedigree data to be summarized into an overall probability of descent of a desirable phenotype. This permits a much more efficient analysis while still using as much available data as possible, thereby increasing the predictive accuracy, as all markers that show a predictive effect are part of the analysis, even if not otherwise statistically significant for traditional QTL analysis.

The disclosed method can also be used to calculate the parental dissimilarity at a locus in the form of the actual or the effective number of the latent ancestral classes. It is impossible to detect a QTL at loci for which the effective number is close to 1. The uncertainty about the inheritance of a particular individual in the set of individuals under consideration is provided by $1 - 1/n_{\textit{eff},i}$.

The present invention is further illustrated by the following examples. The foregoing and following description of the present invention and the various embodiments are not intended to be limiting of the invention but rather are illustrative thereof. Hence, it will be understood that the invention is not limited to the specific details of these examples.

Example 1

Description of Classification Method

The identity-by-descent matrix Q is a square matrix containing a measurement of the similarity between two individuals. The similarity measurement may be the probability that any two individuals share the same allele of a common ancestor for a particular gene, marker, chromosomal segment, or haplotype. Equivalently, the Q matrix could have values that are an average similarity measure (possibly weighted) across specific genomic segments or the whole genome. The values within the Q matrix are determined by collecting pedigree and genotype information on individuals in a population. The number of ancestral alleles is unknown. An example of such a matrix is shown in Table 2 for 8 individuals labeled A-H.

A latent ancestor model with K disjoint latent classes in which each individual belongs to precisely one latent class is an example method for assigning the individuals in Table 2 into groups. The crisp class memberships in latent class models can also be extended to probabilistic measures. Let P be a matrix with elements $p_{ik}$ being the probability that individual i belongs to class k for i=1 ... n individuals and k=1 ... K classes (see Eq. (1)).

Finding the matrix P that solves $Q \approx PP^T$ where P has non-negative elements is one way to classify Q. Solving this equation by one of the algorithms outlined above yields the matrix in Table 3 with K=5. The columns of P in Table 3 are arranged in order of decreasing column sums. Note that the diagonal elements in $PP^T$ are ignorable for the minimization problem. The approximation to Q is very good (RMSE=0.0001).

We now provide examples of the interpretation of statistics derived from the matrix P. In Table 3, four individuals can inherit from ancestor F1 but the expected number of individuals that inherit from class F1 (the column sum for F1) is only 2.98, because of the low probability for individual B and the less than 1 probability for individual E. The expected number of individuals that inherit from the last class, F5, is only 0.006. As a result, the measures for parental dissimilarity in this example, namely the actual and effective number of latent ancestral classes, are 5 and 3.08, respectively. For individual H, the actual and effective number of latent ancestral classes are 2 and 1.47, respectively. The uncertainty about the inheritance of this particular individual in the set of individuals under consideration is $1-1/n_{\textit{eff},i}=0.32$, which the maximum of the inheritance uncertainties for the individuals in Table 3. The inheritance uncertainty is zero for individuals A, C, D and F.

Another method for classifying individuals can occur via a threshold method that yields a binary model for Q. Transform the matrix Q into a discrete matrix S by applying the rule that $s_{ij}=0$ if $q_{ij}<t$ and otherwise $s_{ij}=1$. The variable t is the threshold and $s_{ij}$ is the identity-by-descent status for individuals i and j. Using t=0.6 to the Q matrix in Table 2 yields a binary P matrix with three groups (F1, F2, F3) of individuals as shown in Table 4. Many other possible methods documented in the literature (e.g., Shepard and Arabie (1979), Sato and Sato (1994)), could be used for assigning individuals from Table 2 into groups but we do not describe those methods in detail here.

TABLE 2

Identity by descent matrix for 8 individuals labeled A-H where number of ancestral alleles is unknown.

| Individual | A | B | C | D | E | F | G | H |
|---|---|---|---|---|---|---|---|---|
| A | 1 | 0.032 | 1 | 0 | 0.950 | 0 | 0 | 0 |
| B | 0.032 | 1 | 0.032 | 0.892 | 0.034 | 0.069 | 0.056 | 0.234 |
| C | 1 | 0.032 | 1 | 0 | 0.950 | 0 | 0 | 0 |
| D | 0 | 0.892 | 0 | 1 | 0 | 0 | 0 | 0.200 |
| E | 0.950 | 0.034 | 0.950 | 0 | 1 | 0.050 | 0.040 | 0.040 |
| F | 0 | 0.069 | 0 | 0 | 0.050 | 1 | 0.810 | 0.800 |
| G | 0 | 0.056 | 0 | 0 | 0.040 | 0.810 | 1 | 0.648 |
| H | 0 | 0.234 | 0 | 0.200 | 0.040 | 0.800 | 0.648 | 1 |

TABLE 3

Classification of individuals in Table 2 using a latent ancestor model.

| Individual | F1 | F2 | F3 | F4 | F5 |
|---|---|---|---|---|---|
| A | 1 | 0 | 0 | 0 | 0 |
| B | 0.032 | 0.069 | 0.892 | 0.001 | 0.006 |
| C | 1 | 0 | 0 | 0 | 0 |
| D | 0 | 0 | 1 | 0 | 0 |
| E | 0.950 | 0.050 | 0 | 0 | 0 |
| F | 0 | 1 | 0 | 0 | 0 |
| G | 0 | 0.810 | 0 | 0.190 | 0 |
| H | 0 | 0.800 | 0.200 | 0 | 0 |

TABLE 4

Classification of individuals using a threshold method.

| Individual | F1 | F2 | F3 |
|---|---|---|---|
| A | 1 | 0 | 0 |
| B | 0 | 0 | 1 |
| C | 1 | 0 | 0 |
| D | 0 | 0 | 1 |
| E | 1 | 0 | 0 |
| F | 0 | 1 | 0 |
| G | 0 | 1 | 0 |
| H | 0 | 1 | 0 |

Example 2

Application to Selection of Populations

The proposed invention may be used to select individuals for use in a breeding program as the parents of new populations.

Table 5 considers a set of existing information on the relative breeding value of two maize chromosomal segments. The first segment can be traced to three different ancestral individuals, labeled white, grey, or black. These ancestral founders of the current breeding population have known a priori qualitative breeding values of good, average, and poor, respectively, for a given trait. At another genetic locus the same three founder individuals are present but with a different set of breeding values. Although this example uses only three founder individuals it should be obvious that the method can be extended to arbitrary numbers of founders and traits and that other breeding value ranking systems could be used, such as quantitative metrics rather than the stylized qualitative metric shown in Table 5. Additionally, and without loss of generality, we will assume that the two loci shown in Table 5 combine together additively.

FIG. 1 shows the position of the two loci as being located on the same chromosome. Additionally, pedigree and genotypic information collected on the founders and 8 individuals (labeled A-H) has been used to generate identity by descent (IBD) data. Many standard techniques for calculating IBD within a population are available in the literature (Meuwissen and Goddard (2007); Mao and Xu (2005); Besnier and Carlborg (2007); Wang et al. (1995); Heath (1997); Pong-Wong et al. (2001)) and customized methods can be built that extend these methods to particular reference populations. FIG. 1 uses the colors white, grey, and black to show which of the three founders these 8 individuals carry on this chromosome.

A Q matrix for the allelic structure of the individuals at these two loci can be constructed. In turn, this information can be used to generate a second matrix indicating the founders of the 8 individuals at the two loci of interest and thus to classify the individuals into groups. For a simple pedigree, in which the founders are also the most recent common ancestors of the individuals, this second matrix is likely to be similar (or even identical) to the 8×3 matrix containing the identity by descent probabilities between each of the individuals and each of the founders. It is thus possible to directly identify the latent ancestors with the known founders of Table 5. Table 6 shows a further classification of the 8 individuals into 5 groups depending on the founders present at locus 1 and at locus 2.

The classification of these 8 individuals into groups, coupled with our knowledge of the breeding value of locus 1 and locus 2, enables the selection of individuals for use in further crosses in the breeding program (Table 6, last column). In this example we show that individuals A, B, C, D, and E were selected for use as parents of new populations since these individuals do not carry the poor allele at either locus. New populations generated from these individuals will be biased toward producing favorable progeny.

This example can be generalized to the case where the founders are unknown and the IBD information is used with the disclosed method to make inferences on the founders. In this case the founders are latent (unknown). The breeding value of the founders, such as in Table 5, can still be determined as in the case that the 8 individuals are a subset of a larger set for which some individuals are phenotyped. This shows the generality of the selection method presented here.

TABLE 5

Breeding values for various founding individuals in a hypothetical population.

| | Breeding Value |
|---|---|
| Locus 1 Founder | |
| White | Good |
| Grey | Average |
| Black | Poor |
| Locus 2 Founder | |
| White | Average |
| Grey | Good |
| Black | Poor |

TABLE 6

Classification of 8 individuals into into 5 groups depending on founders present at locus 1 and 2.

| Individual | Locus 1 IBD | Locus 2 IBD | Group | Select |
|---|---|---|---|---|
| A | White | White | 1 | Yes |
| B | Grey | Grey | 2 | Yes |
| C | Grey | White | 3 | Yes |
| D | Grey | Grey | 2 | Yes |
| E | Grey | Grey | 2 | Yes |
| F | Black | White | 4 | No |
| G | Black | Black | 5 | No |
| H | Black | White | 4 | No |

Example 3

Application to a Biparental Population

The proposed invention may be used to select individuals for use in a breeding program. In this example we detail one application of this approach for selecting individuals from a single biparental cross between two inbred parents.

Figure 2:
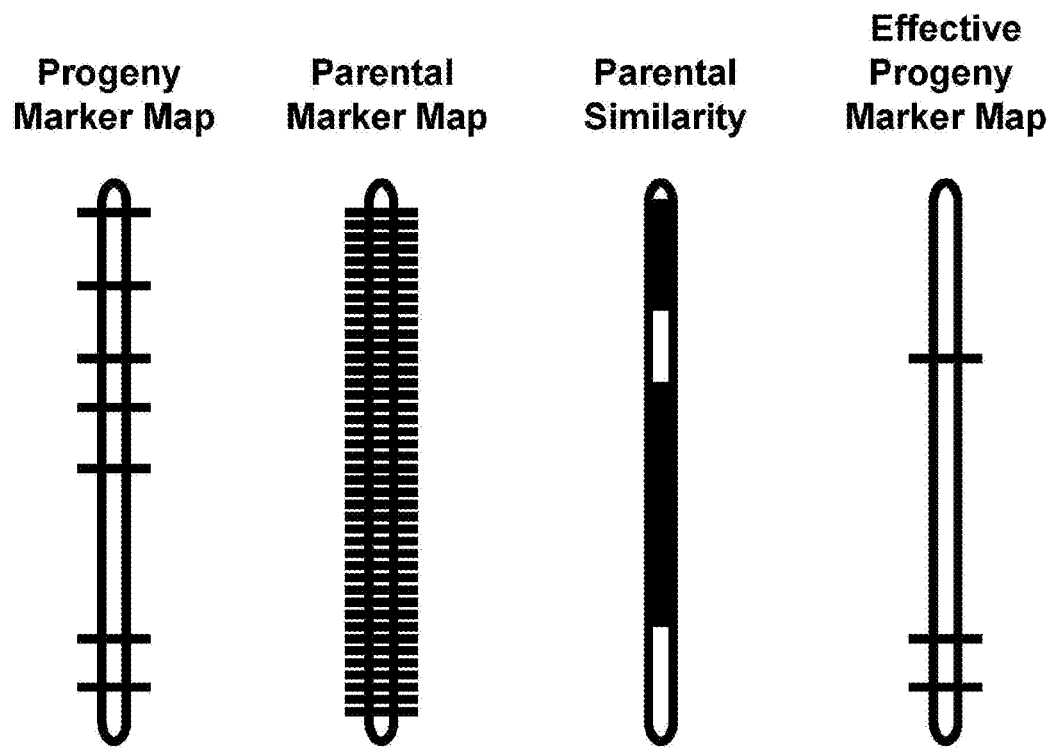
FIG. 2 is a graphical depiction of regions of similarity and difference for the genomes of parental lines, as identified by identity by descent information obtained using a dense parental marker map, and a depiction of the resulting effective progeny marker map.

Identity-by-descent (IBD) information is generated on a population based on pedigree and marker data. Many standard techniques for calculating IBD within a population are available in the literature (Meuwissen and Goddard (2007); Mao and Xu (2005); Besnier and Carlborg (2007); Wang et al. (1995); Heath (1997); Pong-Wong et al. (2001)) and customized methods can be built that extend these methods to particular reference populations. All the available pedigree and genotype information is used to construct the IBD profile for individuals in the population. In this example we show that the parents of the biparental cross have a dense set of marker information available whereas the progeny are genotyped at fewer marker positions. This is a typical situation in commercial plant breeding programs and a schematic representation is shown in FIG. 2. Additionally, the presence of a dense marker set for the parents allows multipoint techniques to be applied. Combining such techniques with accurate pedigree records further improves the IBD calculation through the imputation of missing genotypes and the identification and correction of genotyping and/or pedigree errors.

The IBD information allows us to classify the progeny into groups; multiple methods for performing this classification were described in Example 1. In some parts of the genome the two parents of the progeny have similar IBD information (the black bands in FIG. 2). In these regions all individuals are assigned to a single group as the effective number of latent ancestors is close to 1. That is, all individuals have completely similar genetics for these loci. In regions where the parents differ in their IBD profiles (the white bands in FIG. 2) the alleles of the progeny can be classified into multiple groups based on mating design. For a set of doubled haploid individuals, for example, there are two possible groups for the progeny: individuals may have either the alleles of the first parent or those of the second parent.

The classification of the progeny into groups using highly accurate IBD information is then used to augment a statistical analysis of the progeny. In this example we consider mapping of quantitative trait loci (QTL) as the statistical analysis technique. The classification of the progeny allows us to consider a smaller number of marker positions, termed the effective progeny marker map, rather than the full set of marker loci at which the progeny have been genotyped. The effective progeny marker map is created by not analyzing markers in regions of the genome where no marker polymorphisms can occur. This reduces the computational complexity and potentially speeds up the QTL analysis.

Figure 3:
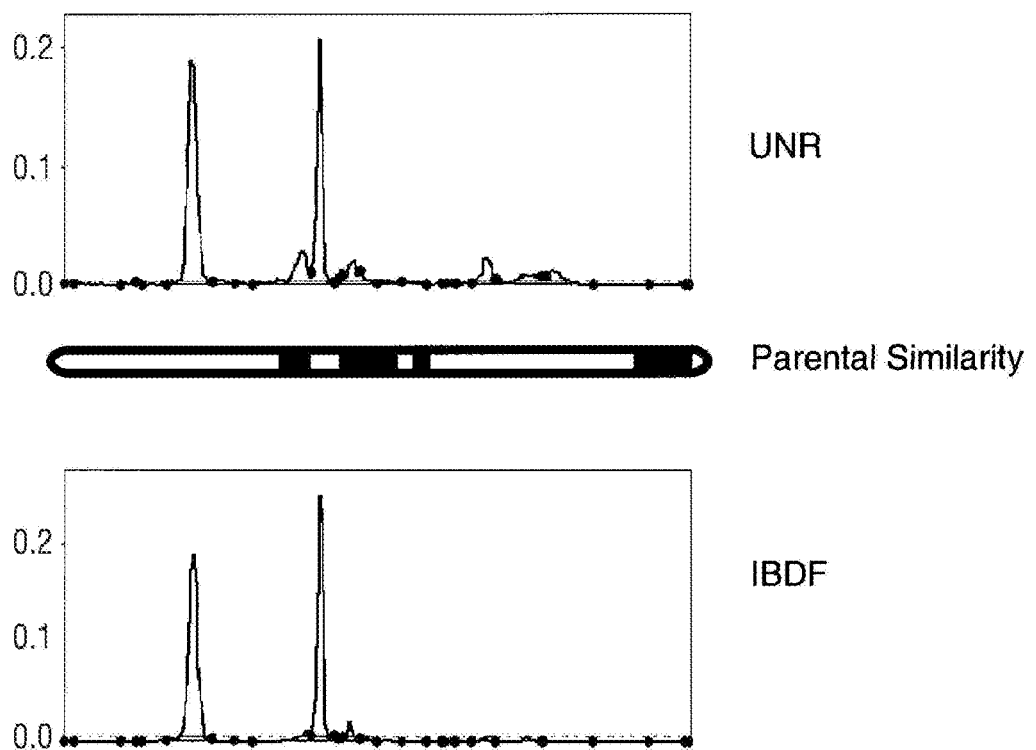
FIG. 3 is the result of a QTL analysis on grain yield data collected on 976 F5 maize topcross progenies at a single location in the United States Corn Belt.

FIG. 3 shows the results of such a QTL analysis on grain yield data collected on 976 F5 maize topcross progenies at a single location in the US corn belt. The data used for this analysis have been extensively described and published on elsewhere (Boer et al. (2007); Openshaw and Frascaroli (1997)). The QTL analysis in this case was conducted using a Bayesian Markov Chain Monte Carlo method (Bink et al. (2002)). In the top panel we see the QTL mapping results along one of ten maize chromosomes that are generated by considering the parents to be unrelated (UNR). Clear QTL signal is identified on this chromosome for grain yield, particularly in two peaks on the top arm of the chromosome. In the bottom panel we have augmented the QTL analysis by considering the relatedness of the two parents to classify the progeny genotypes into groups (IBDF). The genetic similarity between the two parents is shown between the two QTL profiles and clearly identifies regions where the two parents have identical IBD profiles (black bands). A preferred way to quantitatively define the genetic similarity here is $1/n_{\textit{eff}}$ with $n_{\textit{eff}}$ calculated from the second matrix P. For the QTL peak near the middle of the chromosome the inclusion of the IBD information on the parents has allowed the analysis to exclude certain genomic regions as potentially containing the QTL. In this way the QTL profile is much sharper and specific when IBD information is included and provides a better determination of QTL locations. We note that in this instance the overall genetic signal detected in the IBDF approach (i.e. the estimated trait heritability) is similar to that identified when the parents are assumed to be unrelated (Table 7), both for grain moisture at harvest and grain yield.

TABLE 7

Genetic signal detected by IBDF approach and
when parents are assumed to be related.

| $H^2$ | UNR | IBDF |
|---|---|---|
| GRAIN YIELD | 0.10 | 0.16 |
| GRAIN MOISTURE | 0.38 | 0.35 |

Figure 4:
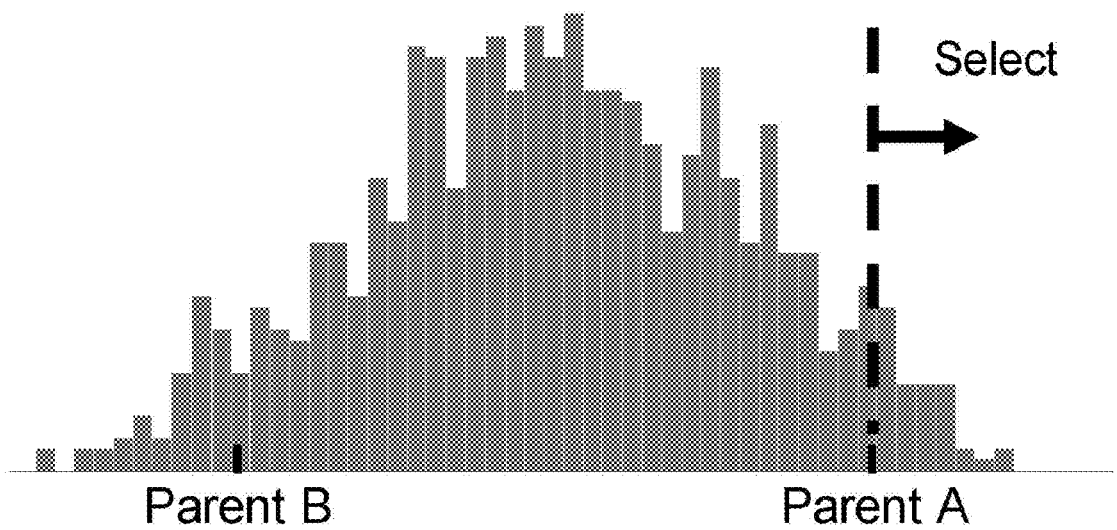
FIG. 4 is a histogram of the estimated genetic value for all 976 progeny obtained by summing the weighted effects of all QTL positions identified on all ten chromosomes.

The identified QTL peaks can then be used to select individuals from the biparental cross for future use in the breeding program. In FIG. 4 we show a histogram of the estimated genetic value for all 976 progeny obtained by summing QTL effects at each of the QTL positions identified on all ten chromosomes. The genetic values of the two inbred parents, labeled A and B in the figure, are shown for reference. The selection of individuals that outperform the yield of the top performing parent is indicated by the dashed vertical line. Other methods for selecting individuals, both on a single or multiple trait basis, may also be used.

Example 4

Application to a Typical Testcross Population in a Breeding Program

The proposed invention may be used to select individuals for use in a breeding program. In this example we detail one application of this approach for selecting individuals from multiple crosses between related inbred parents.

Populations comprised of multiple connected crosses between inbred parents are typical in plant breeding programs (e.g., Blanc et al. (2007)), particularly for the development of new inbred lines. Additionally, the detection of quantitative trait loci responsible for complex trait variation within such populations is of key interest to the scientific community (e.g., U.S. Pat. No. 6,399,855).

The population for this example contained five inbred parents used in four connected crosses of 681 total double haploid maize topcross progeny grown at 12 test locations throughout the United States. The mating design was a half-sib structure around one of the five inbred parents. Phenotypic data were collected on numerous traits using standard practices although only a trait related to maturity date was analyzed for this example.

As described previously, pedigree and genotype information can be collected on the set of parents which have been crossed. This information is used to calculate identity-by-descent (IBD) information on the parents and progeny in the population and in turn used by the methods described in previous examples to classify the progeny into groups (see Example 1 for descriptions of these methods). The resulting information was then used to augment a statistical analysis of the population using Bayesian Markov Chain Monte Carlo methods for mapping quantitative trait loci (QTL; Bink et al., 2002, 2008).

Figure 5:
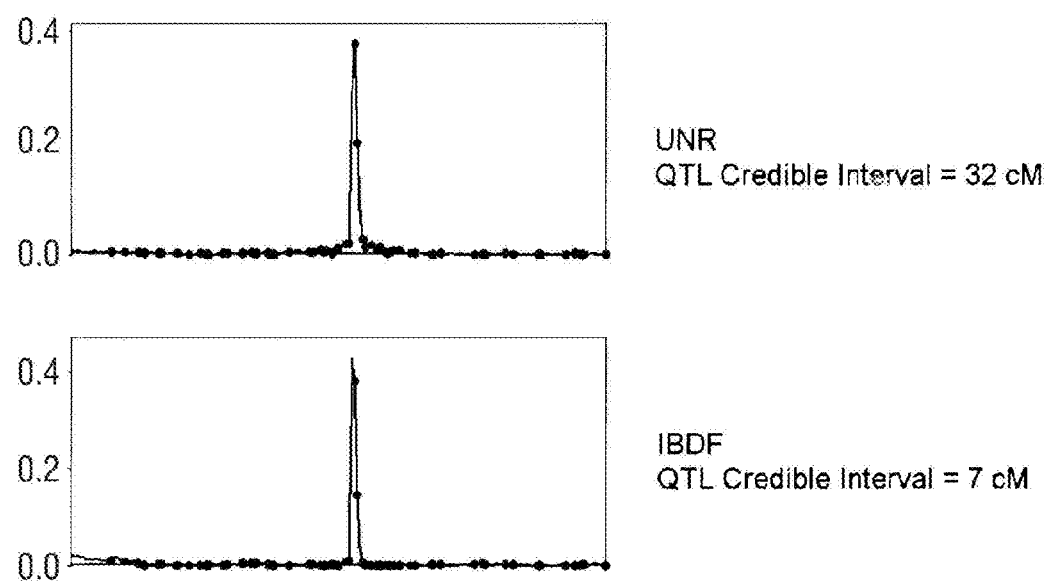
FIG. 5 is a QTL intensity profile from analysis of data where parents are considered to be unrelated and when IBD information is used to augment the analysis.

FIG. 5 shows a QTL intensity profile from the analysis of these data for the case where the parents are considered to be unrelated (UNR, top panel) and when IBD information is used to augment the statistical analysis (IBDF, bottom panel). Clearly both analyses identify genetic signal in similar positions along this particular chromosome. The UNR case, however, presents a wider QTL credible interval (Gelman (2004)) around the peak position. In the UNR case the QTL credible interval was roughly 32 centiMorgans whereas when using IBD information in the manner described by the invention the QTL credible interval is reduced to a region of 7 centiMorgans. The IBDF approach has provided a more precise localization of the QTL that is corroborated by extensive outside evidence, wherein the specific gene associated with the time of flowering in maize, vgt1, has been positionally cloned to a 2 kilobase region on maize chromosome 8 within this interval (Salvi et al. (2007)).

Tables 8-10 help to explain why the IBDF approach was able to locate this QTL more precisely than the UNR case. These tables show a sharply defined region from 118-123 centiMorgans in which the recurrent parent in the half-sib mating design is clearly different from the other four parents. Also, the other four parents are all highly related within this region. Analysis of the phenotypic and marker data, when combined with this information, makes it possible to observe a QTL contrast between parent A and parents B-E within this region. At positions 117 cM and 124 cM, however, parent A does have some relationship to parents B-E, which makes it unlikely that the QTL would reside at those positions. Because of these relationships the QTL analysis in the IBDF case positions the QTL always in the region from 117 cM to 124 cM and thus gives a narrower QTL credible interval. The effective number of ancestral classes is very close to 1 (1.01) for Table 8 whereas this statistic equals 1.47 and 1.31 for Tables 9 and 10, respectively. The P matrices from these Q matrices clearly show that two ancestral classes are highly probable between 118 and 123 cM as well. A chief advantage of using computer methods for determining P is obvious to those skilled in the art, in that human inspection of matrices like Tables 8-10 is impractical for the large volume of marker data available on individuals of interest in a breeding program. Moreover, it should be clear that our method makes the assignment of individuals to groups straightforward for Q matrices with off-diagonal elements intermediate between 0 and 1.

TABLE 8

Q matrix at 117 cM.

| Individual | A | B | C | D | E |
|---|---|---|---|---|---|
| A | 1 | 0.98 | 0.98 | 0.98 | 0.98 |
| B | 0.98 | 1 | 1 | 1 | 1 |
| C | 0.98 | 1 | 1 | 1 | 1 |
| D | 0.98 | 1 | 1 | 1 | 1 |
| E | 0.98 | 1 | 1 | 1 | 1 |

TABLE 9

Q matrix averaged across 118-123 cM.

| Individual | A | B | C | D | E |
|---|---|---|---|---|---|
| A | 1 | 0.01 | 0.01 | 0.01 | 0.01 |
| B | 0.01 | 1 | 1 | 1 | 1 |
| C | 0.01 | 1 | 1 | 1 | 1 |
| D | 0.01 | 1 | 1 | 1 | 1 |
| E | 0.01 | 1 | 1 | 1 | 1 |

TABLE 10

Q matrix at 124 cM.

| Individual | A | B | C | D | E |
|---|---|---|---|---|---|
| A | 1 | 0.31 | 0.31 | 0.31 | 0.31 |
| B | 0.31 | 1 | 1 | 1 | 1 |
| C | 0.31 | 1 | 1 | 1 | 1 |

TABLE 10-continued

Q matrix at 124 cM.

| Individual | A | B | C | D | E |
|---|---|---|---|---|---|
| D | 0.31 | 1 | 1 | 1 | 1 |
| E | 0.31 | 1 | 1 | 1 | 1 |

TABLE 11

P matrix for Q matrix in Table 8.

| Individual | F1 | F2 |
|---|---|---|
| A | 0.98 | 0.02 |
| B | 1 | 0 |
| C | 1 | 0 |
| D | 1 | 0 |
| E | 1 | 0 |

TABLE 12

P matrix for Q matrix in Table 9.

| Individual | F1 | F2 |
|---|---|---|
| A | 0.01 | 0.99 |
| B | 1 | 0 |
| C | 1 | 0 |
| D | 1 | 0 |
| E | 1 | 0 |

TABLE 13

P matrix for Q matrix in Table 10.

| Individual | F1 | F2 |
|---|---|---|
| A | 0.31 | 0.69 |
| B | 1 | 0 |
| C | 1 | 0 |
| D | 1 | 0 |
| E | 1 | 0 |

Example 5

Application to a Typical Set of Hybrids in a Breeding Program

The proposed invention may be used to select individuals for use in a breeding program. In this example we detail one application of this approach for selecting F1 hybrid progeny.

Populations of F1 hybrid progeny are typical of breeding programs as these represent potential products for commercial release. In this example we evaluated a population of 385 F1 hybrids grown in many locations throughout the United States. Phenotypic data were collected on numerous traits using standard practices although only a trait related to maturity date was analyzed for this example. Each F1 hybrid is produced by crossing two inbred parents together.

Pedigree and genotype information was collected on the set of inbred parents that created the hybrid population. In the current example this meant recording up to 18 generations of pedigree relationships and genotypic information at 768 SNP markers throughout the genome. This information was used to calculate identity-by-descent information on the parents and F1 progeny as described in Example 3 and the threshold method described in Example 1 was used to classify the progeny into groups. The resulting matrix was then used to augment a statistical analysis of the F1 progeny using Bayesian Markov Chain Monte Carlo methods (Bink et al. (2002, 2008)).

Figure 6:
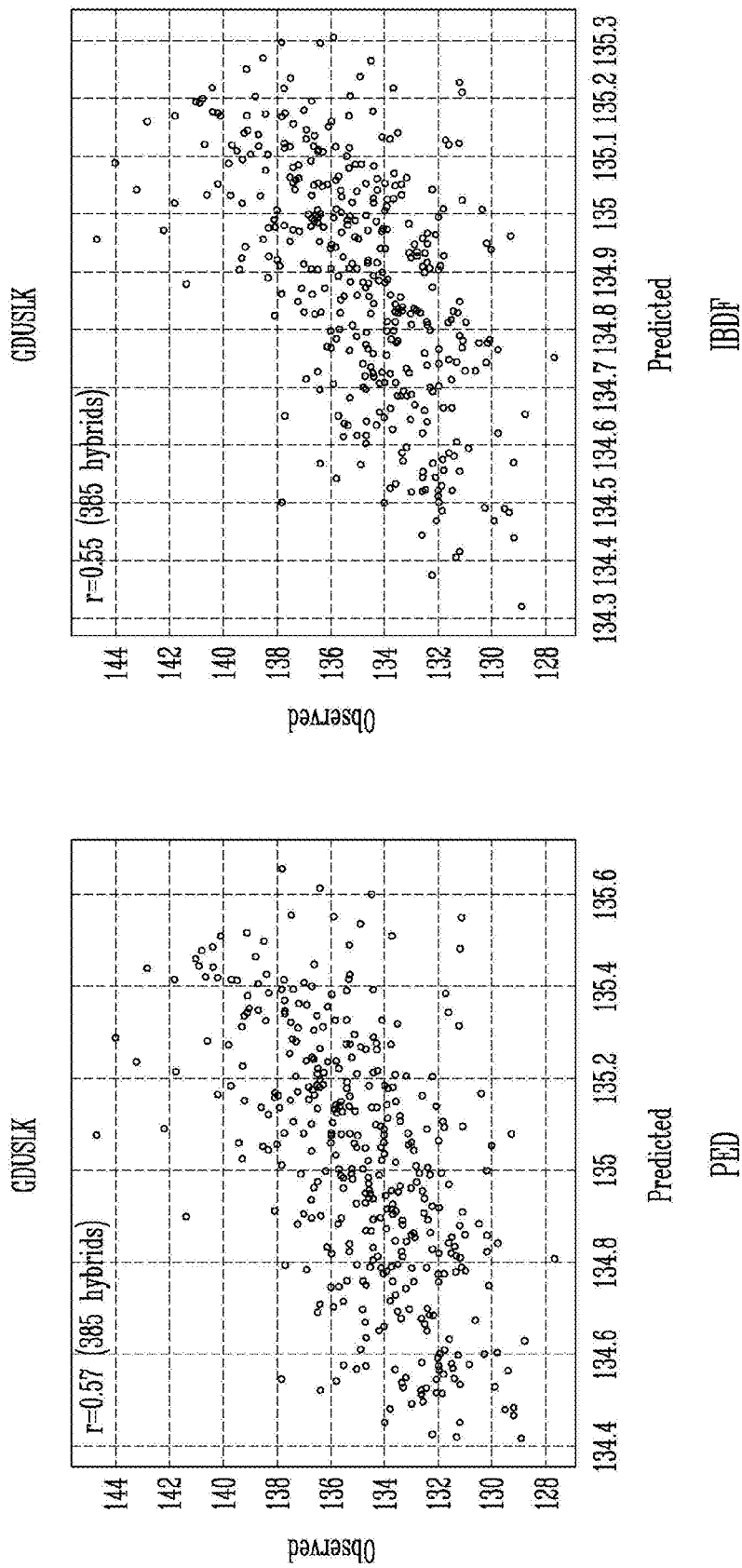
FIG. 6 is a comparison of predicted maturity date when using traditional pedigree-only approaches and when augmenting the analysis using IBD.

A whole genome selection technique was chosen as the statistical technique for evaluating the F1 hybrid progeny (e.g. Meuwissen et al. (2001)). FIG. 6 shows a comparison of the predicted maturity date to their observed maturity date for all 385 hybrids when using traditional pedigree-only approaches (PED, left panel) and when augmenting the statistical analysis (IBDF, right panel). Both analysis methods had correlation coefficients between 0.5 and 0.6 when comparing predictions to observed data for this example. In the IBDF approach, however, the 18 ancestral generations are not included in the analysis because all of those relationships are captured through the IBD matrices that we have used to group the population. This reduces the computational complexity of the analysis and potentially reduces its run-time.

Figure 7:
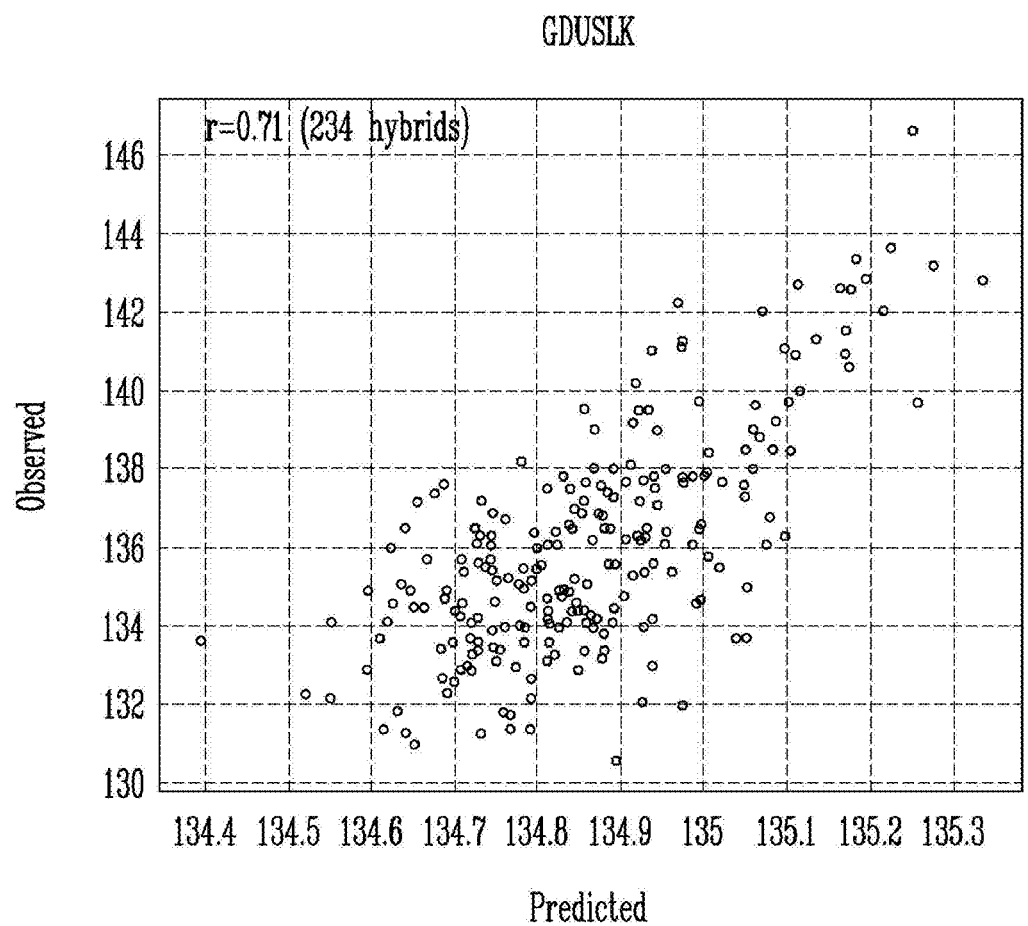
FIG. 7 is a graph comparing predicted values for new selected F1 hybrids to their observed measurements.

In addition the method can be used to choose the parents of new F1 hybrid individuals for the breeding program. The IBDF approach was used to predict genetic values for new, untested hybrid combinations based on the augmented statistical analysis described above. FIG. 7 shows the correlation of the predicted values for the new, selected F1 hybrids compared to their observed measurements in a new experiment. In this example the IBDF approach had a linear correlation coefficient between the predicted and observed values for maturity date of 0.71.

While the foregoing invention has been described in some detail for purposes of clarity and understanding, it will be clear to one skilled in the art from a reading of this disclosure that various changes in form and detail can be made without departing from the true scope of the invention. For example, all the techniques described above can be used in various combinations.

The following references cited herein are hereby expressly incorporated by reference in their entirety:

Besnier F, Carlborg O. A general and efficient method for estimating continuous IBD functions for use in genome scans for QTL. BMC Bioinformatics 2007; 8:440. doi: 10.1186/1471-2105-8-440.

Bink, M. C. A. M., Uimari, P., Sillanpaa, M. J., Janss, L. L. G.; Jansen, R. C., 2002. *Multiple QTL mapping in related plant populations via a pedigree-analysis approach*. Theoretical and applied genetics 104, 751-762.

Bink, M. C. A. M., M. P. Boer, C. J. F. ter Braak, J. Jansen, R. E. Voorrips & W. E. van de Weg, 2008. Bayesian analysis of complex traits in pedigreed plant populations. Euphytica 161: 85-96.

Blanc G, Charcosset A, Veyrieras J B, Gallais A, Moreau L. Marker-assisted selection efficiency in multiple connected populations: a simulation study based on the results of a QTL detection experiment in maize. Euphytica 2008; 161: 71-84.

Boer M, Wright D, Feng L, Podlich D, Luo L, Cooper M, Van Eeuwijk F. A mixed model quantitative trait loci (QTL) analysis for multiple environment trial data using environmental covariables for QTL-by-environment interactions, with an example in maize. Genetics 2007; 177:1801-1813. doi:10.1534/genetics.107.071068.

Gelman, Andrew et. al. *Bayesian Data Analysis* (Chapman & Hall 2004).

Hill, M. O., 1973 Diversity and Evenness—Unifying Notation and Its Consequences. Ecology 54: 427-432.

Heath S C. Markov Chain Monte Carlo Segregation and Linkage Analysis for Oligogenic Models. Am J Hum Genet. 1997; 61:748-760.

Lawson, C. L. and Hanson, R. J., 1974. Solving least squares problems. Prentice-Hall, Englewood Cliffs, N.J.

Lawson, C. L. and Hanson, R. J., 1995. Solving Least Squares Problems. Classics in Applied Mathematics. SIAM, Philadelphia.

Mao Y, Xu S. A Monte Carlo algorithm for computing the IBD matrices using incomplete marker information. Heredity 2005; 94:305-315. doi:10.1038/sj.hdy.6800564.

Malosetti, M, Visser, R G F, Celis-Gamboa, C, and van Eeuwijk, F A. Qtl methodology for response curves on the basis of non-linear mixed models, with an illustratrion to senescence in potato. Theor. Appl. Genet. 2006; 113, 288-300. doi: 10.1007/s00122-006-0294-2.

Meuwissen T H E, Goddard M. Multipoint identity-by-descent prediction using dense markers to map quantitative trait loci and estimate effective population size. Genetics 2007; 176:2551-2560. doi:10.1534/genetics.107.070953.

Meuwissen T H E, Hayes B J, Goddard M E. Prediction of total genetic value using genome-wide dense marker maps. Genetics 2001; 157:1819-1829.

Rosset, S. and Zhu, J., 2007. Piecewise linear regularized solution paths Ann. Statist., 35, 1012-1030.

Openshaw, S., and E. Frascaroli, 1997 QTL detection and marker assisted selection for complex traits in maize. 52nd Annual Corn and Sorghum Industry Research Conference. ASTA, Washington, D.C., pp. 44-53.

Pong-Wong, R., A. W. George, J. A. Woolliams & C. S. Haley 2001. A simple and rapid method for calculating identity-by-descent matrices using multiple markers. Genetics Selection Evolution 33: 453-471.

Salvi S, Sponza G, Morgante M, Tomes D, Niu X, Fengler K, Meeley R, Ananiev E, Svitashev S, Bruggemann E, Li B, Hainey C, Radovic S, Zaina G, Rafalski J A, Tingey S, Miao G H, Phillips R, Tuberosa R. Conserved noncoding genomic sequences associated with a flowering-time quantitative trait locus in maize. PNAS 2007; 104:11376-11381.

Sato M, Sato Y. An additive fuzzy clustering model. 1994, Japanese Journal of Fuzzy Theory and Systems, 6, 185-204.

Shepard R N, Arabie P. Additive clustering: representation of similarities as combinations of discrete overlapping properties. 1979, Pyschological Review, 86, 87-123.

Wang T, Fernando R L, Van der Beek S, Grossman M, Van Arendonk J A M. Covarience between relatives for a marked quantitative trait locus. Genet Sel evol. 1995; 27:251-274. doi: 10.1051/gse:19950304.

What is claimed is:

1. A method for producing progeny comprising:
 a. collecting pedigree and genotype information pertaining to one or more loci in at least one individual in a population;
 b. building a first matrix by calculating the probability that alleles present at one or more loci in the one or more individuals are identical by descent in the population, based on the pedigree and genotype information;
 c. using the first matrix to produce a second matrix that classifies one or more individuals from the population;
 d. using the second matrix to select a subset of the individuals from the population that have an increased probability of producing progeny having a targeted goal; and,
 e. breeding the selected individuals;
wherein at least one step of the method is implemented on a computer.

2. The method of claim 1 wherein the population comprises members of a plant species.

3. The method of claim 2 wherein the plant species is maize, wheat, rice, millet, barley, sorghum, rye, soybean, alfalfa, oilseed Brassica, cotton, sunflower, potato, or tomato.

4. The method of claim 2 wherein the progeny are hybrids.

5. The method of claim 1 wherein the targeted goal is improving one or more phenotypes.

6. The method of claim 5 wherein the one or more phenotypes are selected from the group consisting of yield, leaf angle, anthesis-silking interval (ASI), staygreen duration, early growth rate, overall growth rate, growth pattern, maximum biomass, total biomass, nitrogen use efficiency, water use efficiency, tocol content, oleic acid content, phytic acid content, amino acid composition, oil quality or quantity, energy availability, digestibility, fatty acid composition, a pathogen defense mechanism, lysine and sulfur levels, starch synthesis, disease resistance, herbicide resistance, male sterility, plant vigor, nutrient content, hemicellulose content, cellulose production, cold tolerance, salt tolerance, heat tolerance, drought tolerance, grain moisture content, stalk lodging, root lodging, root pulling resistance, stand establishment, emergence, midsilk, test weight, protein content, starch percentage, relative maturity, plant height, seed size, disease resistance genes, heading date, resistance to insects, brittle snap, stalk breakage, resistance to fungus, seed moisture, head shape, hullability, seedling vigor, beginning bloom date, maturity date, seed shatter, winter survival, fiber strength, ear height, plant barrenness, seed number, seed weight, and color grade.

7. The method of claim 1 wherein the first matrix is calculated using one or more of the group consisting of stochastic algorithms, deterministic algorithms, maximum likelihood algorithms, and descent graph methods.

8. The method of claim 1 wherein the second matrix is calculated by grouping individuals that exceed a threshold on the entries of the first matrix in a manner that enforces transitivity of group membership.

9. The method of claim 1 wherein the second matrix is calculated using a latent class model, a non-negative matrix factorization model, or a bilinear model.

10. A method for producing selected progeny comprising:
 a. collecting pedigree and genotype information pertaining to one or more loci from a population;
 b. building a first matrix by calculating the probability that alleles present at the one or more loci in one or more individuals are identical by descent in the population, based on the pedigree and genotype information;
 c. using the first matrix to produce a second matrix that assigns one or more individuals from the population into groups;
 d. using the second matrix to augment a statistical analysis of at least one phenotype of progeny of the individuals; and
 e. selecting individuals for use in a breeding program based on the augmented statistical analysis, thereby producing selected progeny;
wherein at least one step of the method is implemented on a computer.

11. The method of claim 10 wherein the population comprises members of a plant species.

12. The method of claim 11 wherein the plant species is maize, wheat, rice, millet, barley, sorghum, rye, soybean, alfalfa, oilseed Brassica, cotton, sunflower, potato, or tomato.

13. The method of claim 11 wherein the progeny are hybrids.

14. The method of claim 11 wherein the at least one phenotype is selected from the group consisting of yield, leaf angle, anthesis-silking interval (ASI), staygreen duration, early growth rate, overall growth rate, growth pattern, maximum biomass, total biomass, nitrogen use efficiency, water use efficiency, tocol content, oleic acid content, phytic acid content, amino acid composition, oil quality or quantity, energy availability, digestibility, fatty acid composition, a pathogen defense mechanism, lysine and sulfur levels, starch synthesis, disease resistance, herbicide resistance, male sterility, plant vigor, nutrient content, hemicellulose content, cellulose production, cold tolerance, salt tolerance, heat tolerance, drought tolerance, grain moisture content, stalk lodging, root lodging, root pulling resistance, stand establishment, emergence, midsilk, test weight, protein content, starch percentage, relative maturity, plant height, seed size, disease resistance genes, heading date, resistance to insects, brittle snap, stalk breakage, resistance to fungus, seed moisture, head shape, hullability, seedling vigor, beginning bloom date, maturity date, seed shatter, winter survival, fiber strength, ear height, plant barrenness, seed number, seed weight, and color grade.

15. The method of claim 10 wherein the first matrix is calculated using one or more of the group consisting of stochastic algorithms, deterministic algorithms, maximum likelihood algorithms, and descent graph methods.

16. The method of claim 10 wherein the second matrix is calculated by grouping individuals that exceed a threshold on the entries of the first matrix in a manner that enforces transitivity of group membership.

17. The method of claim 10 wherein the second matrix is calculated using a latent class model, a non-negative matrix factorization model, or a bilinear model.

* * * * *